US009247990B2

(12) United States Patent
Kauphusman et al.

(10) Patent No.: US 9,247,990 B2
(45) Date of Patent: Feb. 2, 2016

(54) STEERABLE SHEATH ACCESS DEVICE

(75) Inventors: James V. Kauphusman, Camplin, MN (US); Allan M. Fuentes, Mound, MN (US); Troy T. Tegg, Elk River, MN (US); Dale E. Just, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 393 days.

(21) Appl. No.: 13/350,471

(22) Filed: Jan. 13, 2012

(65) Prior Publication Data

US 2012/0108938 A1    May 3, 2012

Related U.S. Application Data

(63) Continuation of application No. 12/442,196, filed as application No. PCT/US2007/080939 on Oct. 10, 2007, now Pat. No. 8,814,824.

(60) Provisional application No. 60/828,939, filed on Oct. 10, 2006.

(51) Int. Cl.
*A61B 18/14* (2006.01)
*A61B 5/042* (2006.01)
(Continued)

(52) U.S. Cl.
CPC .............. *A61B 18/1492* (2013.01); *A61B 5/042* (2013.01); *A61B 5/0422* (2013.01); *A61B 5/6852* (2013.01); *A61M 25/0147* (2013.01); *A61B 18/18* (2013.01); *A61B 18/1815* (2013.01); *A61B 2018/0016* (2013.01); *A61B 2018/00023* (2013.01); *A61B 2018/00029* (2013.01); *A61B 2018/00214* (2013.01); *A61B 2018/00244* (2013.01); *A61B 2018/00285* (2013.01); *A61B 2018/00351* (2013.01); *A61B 2018/00577* (2013.01); *A61B 2018/00839* (2013.01); *A61B 2018/00898* (2013.01); *A61B 2018/1467* (2013.01); *A61B 2018/1497* (2013.01);
(Continued)

(58) Field of Classification Search
CPC .................. A61B 18/1492; A61B 2018/1467; A61B 2017/00243; A61B 2018/1861; A61B 18/082
See application file for complete search history.

(56) References Cited

U.S. PATENT DOCUMENTS 4,890,623 A    1/1990    Cook et al.
5,080,660 A    1/1992    Buelna
(Continued)

FOREIGN PATENT DOCUMENTS

WO    WO-2005/032362    4/2005

OTHER PUBLICATIONS

"Supplementary European Search Report", EP 07844081 Jun. 15, 2011.
(Continued)

*Primary Examiner* — Nathan R Price
*Assistant Examiner* — Weng Lee
(74) *Attorney, Agent, or Firm* — Dykema Gossett PLLC

(57) ABSTRACT

The present invention relates to steerable access sheath assembly including at least one electrode. Moreover, the present invention relates to a steerable sheath access device for use in cardiovascular procedures. Embodiments of the present invention including steerable access sheaths or introducers may provide cardiovascular access for various ablation tools and devices for the performance of various ablation procedures or procedures involving alternate energy sources.

21 Claims, 7 Drawing Sheets

(51) Int. Cl.
- *A61B 5/00* (2006.01)
- *A61M 25/01* (2006.01)
- *A61B 18/18* (2006.01)
- *A61B 18/00* (2006.01)
- *A61N 7/02* (2006.01)

(52) U.S. Cl.
CPC ..... *A61B2560/066* (2013.01); *A61B 2562/222* (2013.01); *A61N 7/02* (2013.01); *Y10T 29/4913* (2015.01)

(56) References Cited

U.S. PATENT DOCUMENTS

| | | | | |
|---|---|---|---|---|
| 5,318,525 | A | * | 6/1994 | West et al. ............. 604/95.04 |
| 5,348,554 | A | | 9/1994 | Imran et al. |
| 5,403,311 | A | | 4/1995 | Abele et al. |
| 5,456,682 | A | | 10/1995 | Edwards et al. |
| 5,476,495 | A | * | 12/1995 | Kordis et al. ............. 607/122 |
| 5,571,085 | A | | 11/1996 | Accisano |
| 5,681,282 | A | | 10/1997 | Eggers et al. |
| 5,683,366 | A | | 11/1997 | Eggers et al. |
| 5,728,094 | A | | 3/1998 | Edwards |
| 5,755,766 | A | * | 5/1998 | Chastain et al. ............. 607/122 |
| 5,766,153 | A | | 6/1998 | Eggers et al. |
| 5,785,705 | A | | 7/1998 | Baker |
| 5,797,903 | A | | 8/1998 | Swanson et al. |
| 5,843,152 | A | | 12/1998 | Tu et al. |
| 5,885,238 | A | * | 3/1999 | Stevens et al. ............. 604/6.14 |
| 5,954,665 | A | | 9/1999 | Ben-Haim |
| 6,015,407 | A | | 1/2000 | Rieb et al. |
| 6,117,088 | A | | 9/2000 | Kreizman et al. |
| 6,168,593 | B1 | | 1/2001 | Sharkey et al. |
| 6,210,406 | B1 | | 4/2001 | Webster |
| 6,226,554 | B1 | | 5/2001 | Tu et al. |
| 6,277,107 | B1 | | 8/2001 | Lurie et al. |
| 6,394,956 | B1 | | 5/2002 | Chandrasekaran et al. |
| 6,494,880 | B1 | | 12/2002 | Swanson et al. |
| 6,517,477 | B1 | | 2/2003 | Wendlandt |
| 6,544,215 | B1 | * | 4/2003 | Bencini et al. ............. 604/95.01 |
| 6,554,794 | B1 | | 4/2003 | Mueller et al. |
| 6,602,242 | B1 | | 8/2003 | Fung et al. |
| 6,726,677 | B1 | | 4/2004 | Flaherty et al. |
| 6,743,239 | B1 | | 6/2004 | Kuehn et al. |
| 6,945,956 | B2 | | 9/2005 | Waldhauser et al. |
| 7,717,899 | B2 | * | 5/2010 | Bowe et al. ............. 604/525 |
| 2001/0007070 | A1 | * | 7/2001 | Stewart et al. ............. 606/41 |
| 2002/0029030 | A1 | | 3/2002 | Lurie et al. |
| 2002/0111618 | A1 | | 8/2002 | Stewart et al. |
| 2002/0128639 | A1 | | 9/2002 | Pless et al. |
| 2002/0165537 | A1 | | 11/2002 | Kelley et al. |
| 2003/0050637 | A1 | | 3/2003 | Maguire et al. |
| 2003/0114832 | A1 | | 6/2003 | Kohler et al. |
| 2003/0181900 | A1 | | 9/2003 | Long |
| 2004/0030331 | A1 | | 2/2004 | Thomas et al. |
| 2004/0143256 | A1 | | 7/2004 | Bednarek |
| 2005/0065508 | A1 | | 3/2005 | Johnson et al. |
| 2005/0159799 | A1 | | 7/2005 | Daglow et al. |
| 2005/0234436 | A1 | | 10/2005 | Baxter et al. |
| 2005/0272975 | A1 | | 12/2005 | McWeeney et al. |
| 2006/0100618 | A1 | | 5/2006 | Chan et al. |
| 2007/0179486 | A1 | | 8/2007 | Welch et al. |
| 2010/0094279 | A1 | | 4/2010 | Kauphusman et al. |
| 2012/0029334 | A1 | * | 2/2012 | Tegg ............. 600/373 |

OTHER PUBLICATIONS

"Supplemental European Search Report", EP 07 84 4086 Jun. 6, 2011.

Hammill, Stephen C., "Epicardial Ablation: Reducing the Risks", *Cardiovasc Electrophysiol*, vol. 17 May 2006, 550-552.

Schweikert, Robert A. et al., "Percutaneous Pericardial Instrumentation for Endo-Epicardial Mapping of Previously Failed Ablations", *Circulation* 2003:108 Sep. 2, 2003, 1329-1335.

Extended European Search Report for EP Application No. 15159972. 7, dated Jul. 1, 2015. 8 pgs.

* cited by examiner

STEERABLE SHEATH ACCESS DEVICE

CROSS-REFERENCE TO RELATED APPLICATIONS

This application is a continuation of U.S. application Ser. No. 12/442,196, filed 10 Oct. 2007, now pending (the '196 application), which is the national stage of International application no. PCT/US2007/080939, with an international filing date of 10 Oct. 2007 (the '0939 application), now abandoned, which claims the benefit of U.S. provisional application No. 60/828,939, filed 10 Oct. 2006 (the '8939 application). The '196 application, the '0939 application, and the '8939 application are all hereby incorporated by reference as though fully set forth herein.

BACKGROUND OF THE INVENTION a. Field of the Invention

The present invention relates to sheaths or introducers. More particularly, the present invention relates to a steerable short sheath access device or introducer for use in epicardial procedures, such as those used for the treatment of atrial fibrillation and ventricular tachycardias.

b. Background Art

Many medical procedures require the introduction of specialized medical devices into and/or around the human heart. In particular, there are a number of medical procedures that requires the introduction of specialized devices, including but not limited to catheters, dilators, and needles, to areas such as into the pericardial sac surrounding the heart in order to access the epicardial or outer surface of the heart. Catheters and access sheaths or introducers have been used for medical procedures for a number of years. It is necessary for introducers and catheters to exhibit a degree of flexibility to be able to maneuver through the vasculature of a patient during the performance of cardiac procedures. In addition, various configurations of introducers are necessary for the treatment of different cardiac conditions.

Atrial fibrillation and ventricular tachycardias are cardiac arrhythmias that result in an irregular heartbeat due to the irregular conduction of electrical impulses to the ventricles of the heart. It is believed that one method of treating atrial fibrillation is through the locating, accessing, stimulating, and ablation of epicardial neuroganglia. It is believed that atrial fibrillation can be controlled more completely by ablating neuroganglia heads located under (or inside) fat pads located on the epicardial surface of the heart. The fat pads are located at the junctions of the pulmonary veins, the inferior vena cava, and in the margin between the aorta and the superior vena cava, all of which may in fact be a major source of fibrillation. Current treatments that involve ablating alternate pathways internal to the heart may be ineffective in truly reaching neuroganlia and instead targets the legs of the neuroganglia, which can necessitate multiple ablations. As a result it is desirable to develop a method of targeting the neuroganlia heads so that the entire circuit can be resolved by ablating the head embedded in or below the fat pad.

In order to ablate the head of the fat pad located on the epicardial surface, it is necessary to use an ablation catheter that is able to access the epicardial surface of the heart. Traditional approaches to treating atrial fibrillation include the use of introducers or catheter systems that are inserted within the internal chambers of the heart to target areas for ablation. Traditional catheters and access devices, such as introducers, access these endocardial areas through a rigid elongated body that includes a curved portion for accessing areas of the heart and related vasculature for ablation. These traditional catheters and access devices can be too long in length to be used in certain pericardial procedures such as that for potential treatment of atrial fibrillation. Moreover, these traditional devices are not able to be maneuvered or steered to reach the epicardial surfaces for treatment or they may have to be curved throughout the pericardial sac and around the heart to reach the tissue areas of interest.

BRIEF SUMMARY OF THE INVENTION

The present invention is directed to steerable access sheaths or introducers. More particularly, the present invention relates to a steerable short sheath access device or introducer for use in epicardial procedures, such as those used for the treatment of atrial fibrillation. Embodiments of the present invention including shorter steerable access sheaths or introducers may provide epicardial access for various ablation tools and devices for the performance of various ablation procedures or procedures involving alternate energy sources. The steerable access device provides an elongated member that exhibits primary and secondary curvatures for access to ablative surfaces or targets.

Accordingly, embodiments of the present invention provide a steerable sheath access device. The access sheath includes an elongated member having a proximal end, a distal end, and a lumen. The lumen of the elongated member extends through the elongated member from the proximal end to the distal end. The elongated member further includes a proximal section made of a first material and a distal section made of a second material. The first material of the proximal section is more rigid than the second material of the distal section. Accordingly, when in use, the distal section may be deflected to provide a primary curve that may further result in a secondary curve of proximal member. The inside radius of curvature of the primary curve is less than the inside radius of curvature of the secondary curve.

Embodiments of the present invention further provide a steerable sheath access device assembly. The assembly includes an elongated member having a proximal end, a distal end, and a lumen. The lumen extends through the elongated member from the proximal end to the distal end. The elongated member further includes a proximal section made of a first material and a distal end made of a second material. The first material of the proximal section is more rigid than the second material of the distal section, such the distal section may be deflected to provide a primary curve that further results in a secondary curve of proximal member. The inside radius of curvature of the primary curve is less than the inside radius of curvature of the secondary curve. The assembly of the present invention further includes a handle assembly defining an outer body portion having a proximal end and a distal end. The distal end of the handle assembly is coupled to the proximal end of the elongated member. The handle assembly further includes a deflection handle portion for controlling the deflection and movement of the elongated member. The handle assembly further includes an inner cavity which extends along the length of the handle assembly. The inner cavity may receive or connect to various tools, such as a catheter, dilator, needle or any other necessary device that is provided through the access sheath. The device assembly further includes a valve assembly having an opening that is coupled to the inner cavity of the handle assembly and the lumen of the elongated member therein providing a passageway.

Further, embodiments of the present invention further provide ablation assemblies that may include, for example, steerable access device assemblies such as those described above. The ablation assembly may further include a dilator for insertion into the passageway of the steerable sheath access device assembly. The ablation assembly further includes an ablation catheter comprising a catheter shaft and an ablation electrode for insertion into the passageway defined by the steerable sheath access device assembly. The ablation assembly may also include a needle for insertion through the steerable sheath access device; and a guidewire for use in positioning the steerable sheath access device assembly.

Accordingly, steerable short sheath access devices as provided by the present invention, as well as the related assemblies, may be provided to enhance and perform the method of ablating epicardial surface for the treatment of atrial fibrillation and ventricular tachycardias.

The foregoing and other aspects, features, details, utilities, and advantages of embodiments of the present invention will be apparent from reading the following description and claims, and from reviewing the accompanying drawings.

DETAILED DESCRIPTION OF THE INVENTION

In general, the present invention relates to a steerable short sheath access device or introducer for use in epicardial procedures, such as those used for the treatment of atrial fibrillation and ventricular tachycardia. The steerable access device provides an elongated member that exhibits primary and secondary curvature for access, for example, to epicardial surfaces for performing ablation. For purposes of this description, similar features among the various embodiments described herein will be referred to by the same reference number. As will be appreciated, however, the structure of the various aspects may differ with respect to alternate embodiments.

The steerable access device, or introducer, of the present invention may be shorter in length than the traditional access devices to provide more effective access to the epicardial surface of the heart through the pericardial sac. In an embodiment, a steerable access device is comprised of a flexible elongated member that can readily reflect or adapt or conform to the curvature or profile of organs, such as the heart, therein defining a gradual curvature of the sheath for positioning the access device within the pericardial sac and ultimately in relation to the epicardial target surface of the heart for performance of various procedures.

Figure 1:
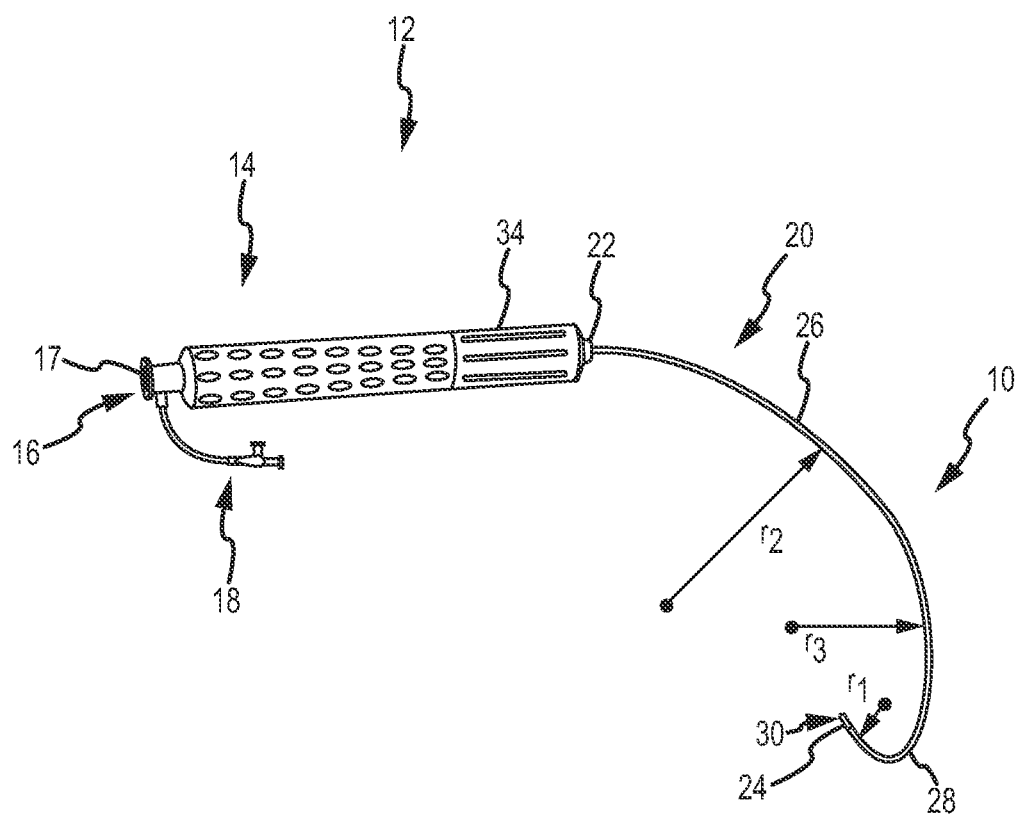
FIG. 1 is an isometric view of steerable sheath access device according to an embodiment of the present invention.

As generally shown in the embodiment illustrated in FIG. 1, the sheath access device 10 may comprise part of a steerable sheath access device assembly 12. The steerable sheath access device assembly 12 may be configured to facilitate access to the epicardial surface of the heart through the pericardial sac. Alternately, assembly 12 may be used, for example, for a number of different procedures. In an embodiment, the steerable sheath access device assembly 12 includes sheath access device 10 connected to a handle assembly 14 for controlling the deflection and movement of device 10, and may further include a valve assembly 16 for allowing introduction of medical device components through aperture 17 accessing inner cavity (not shown) of handle assembly 14, as well as a stopcock 18 that may be used to restrict the flow of liquid or gas through assembly 12 or to flush the assembly to disperse trapped air. FIGS. 2-12 below, describe alternate embodiments and illustrate exemplary applications of sheath access device 10.

Figure 2:
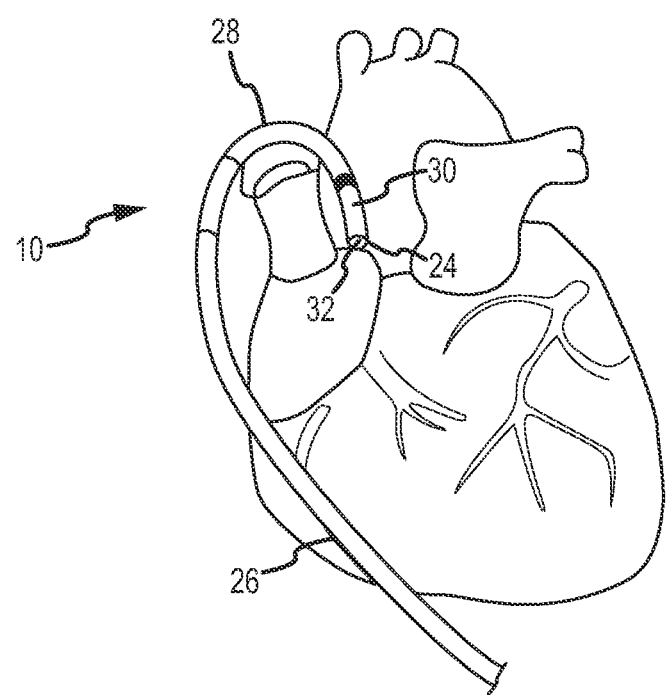
FIGS. 2-4 are illustrative views of the steerable sheath access device positioned in relation to the epicardial surface of the heart during an ablation procedure.
Figure 3:
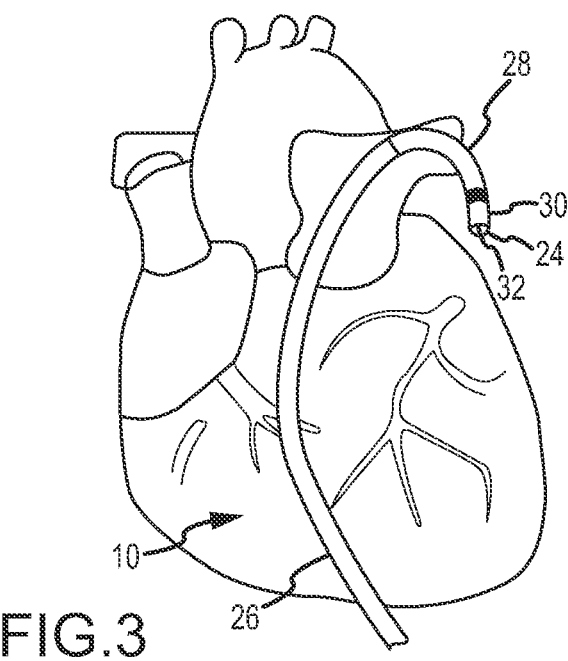
Figure 4:
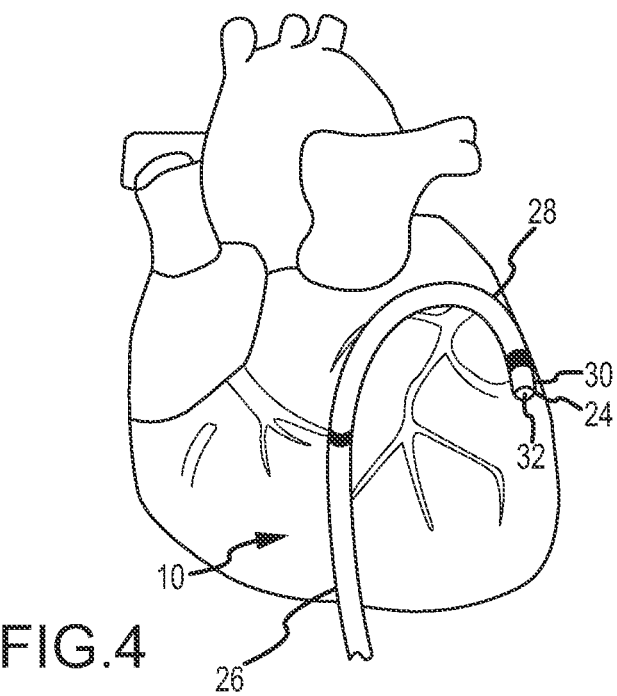

In accordance with an embodiment, as generally illustrated in FIG. 1, sheath access device 10 may be connected to handle assembly 14 as part of steerable sheath access device assembly 12. Sheath access device 10, also often referred to as an introducer, comprises an elongated member 20. Elongated member 20 includes a proximal end 22 and a distal end 24. Elongated member 20 further includes an inner lumen 32, e.g. as shown in FIGS. 2-4, that provides for the insertion and positioning of various medical tools and devices, including but not limited to, catheters, dilators, electrode tips for ablation, needles, and guide wires. Access sheath 10 facilitates the introduction and positioning of devices to establish contact with targeted tissue areas, such as the epicardial surface of the heart within the pericardial sac. Elongated member 20 further includes a proximal section 26 and a distal section 28. Proximal section 26 and distal section 28 may be integral with one another therein providing a single unitary elongated member 20. Moreover, proximal section 26 is positioned more distally with respect to proximal end 22 of elongated member 20 and distal section 28 is positioned more distally with respect to proximal section 26 of elongated member 20. Portions of proximal section 26 and distal section 28 intersect with one another and the components form a unitary sheath 10. Elongated member 10 further includes a distal tip portion 30. Distal tip portion 30 is provided yet further distally with respect to distal section 28 and extends to distal tip 24 of elongated member 20. Distal tip portion 30 may be tapered to form a desirable transition with devices that may be inserted through the inner lumen of elongated member 20. Distal tip 24 may be chamfered to provide a smooth transition end to elongated member 20 of sheath 10 and further provides an outlet for the inner lumen, so that the dilators, catheters, or other devices may exit sheath 10.

Sheath 10 is generally comprised of a biocompatible polymer material that exhibits various degrees of flexibility and rigidity, depending on the design and performance requirements. In an embodiment, elongated member 20 of sheath 10 is comprised of a thermoplastic material, such as, without limitation, PEBAX®. Throughout the length of elongated member 20, various materials such as thermoplastics (e.g. PEBAX®) that exhibit different degrees of hardness (or durometer) may be used, in addition, the material may be braided or provided, in alternate configurations to achieve a desired degree or measure of rigidity and/or flexibility. The device may also be lined with Teflon in order to reduce friction during insertion of various instruments. In an embodiment, proximal section 26 is made of a different material than the material comprising distal section 28, such t hat the hardness or durometer of proximal section 26 is greater than the hardness or durometer of distal section 28. According to an embodiment of the present invention, proximal section 20 may include a hardness/rigidity within the range of 50-70 durometer, For some embodiments the range may be 55-65 durometer. Distal section 28 includes a hardness/rigidity within the range of 35-45 durometer, and may, for example, be about a 40 durometer. In another embodiment, distal tip portion 30 is made of material, such that the hardness /rigidity of distal tip portion 30 is even less than distal section 28. This softness or flexibility can be provided to prevent damage to the pericardial sac and epicardial surface of the heart. Accordingly, distal tip portion 30 may have a hardness/rigidity within the range of 20-30 durometer, and for some embodiments may be approximately 25 durometer , In alternate embodiments, various sections of elongated member 20 may be radiopaque or include various fluorescent markers such that the access sheath is visible through fluoroscopy.

Variations in size and shape of sheath 10 may be used and are intended to encompass all applicable uses, including use on pediatric patients, as well as in adult human hearts. It is recognized that based on the application of device 10, the length of elongated member 20 may vary slightly to reflect the size of the patient being treated. Sheath 10, in accordance with the present invention, is generally 12-17 inches in length. For some embodiments, sheath 10 may be about 17 inches in length. Accordingly, the length of proximal section 26 ranges from about 13.5 inches to about 15.5 inches. For some embodiments, proximal section 26 is approximately 14.5±0.5 inches in length. Distal section 28 ranges from about 1.5 inches to about 3.5 inches. For some embodiments, distal section 28 is approximately 2.5±0.1 inches in length. Slight variations may be made to the length depending on the design or manufacturing of the system. Distal tip portion 30 is further provided and is only approximately 0.125-0.145 inches in length. For some embodiments, distal tip portion 30 is about 0.145 inches in length.

As further seen in FIG. 1 and in accordance with an embodiment of the present invention, sheath 10 includes two curves as provided by proximal section 26 and distal section 28 of elongated member 20. The curvatures may be created or formed via either one set or a plurality of sets of pull wires that run or extend along the length of elongated member 20 and are controlled by mechanisms provided within handle assembly 14. In one embodiment, for example, as shown in FIG. 1, distal section 28 ma include a primary curve that has an inner radius($r_1$) that ranges from about 0.5 to about 2.0 centimeters depending on the deflection forces created or imparted by the user through the use of handle assembly 14. In an embodiment, the inner radius ($r_1$) is about 1.0 centimeter. Proximal section 26 further defines a secondary curve that includes an inner radius ($r_2$) that is substantially greater than the inner radius of the primary curve of distal section 28. As seen in FIG. 1, the secondary curve may also further includes a second inner radius ($r_3$) as further provided by a portion of the secondary curve. The arc or overall curve of the secondary curve of proximal section 26 may vary slight such that multiple radi (r) may define the radius of curvature of the secondary curve. Overall, and in accordance with the embodiments of the present invention, the inner radi ($r^2, r_3$) of the secondary curve provided by proximal section 26 are each substantially greater than (e.g., at least 3, 4, or more times) the inner radius ($r_1$) of the primary curve provided by distal section 28.

As seen in FIGS. 2-4, illustrative views of steerable sheath access device 10 positioned in relation to the epicardial surface of the heart during an ablation procedure are provided. Each of the Figures illustrate the various degrees of curvature of t he proximal sections 26 and distal sections 28 as required during the performance and operation of the sheath access device 10. As can further be seen in comparing FIGS. 2-3 with FIG. 4, as the inner radius of the primary curve decreases and creates a tighter curve, t he inner radius of the secondary curve also decreases, although at a much lesser degree. Accordingly, as the distal section 28 is deflected by the tension applied to pull wires provided throughout elongated member 20, this results in the formation of or increase in secondary curve of proximal section 26.

Figure 5:
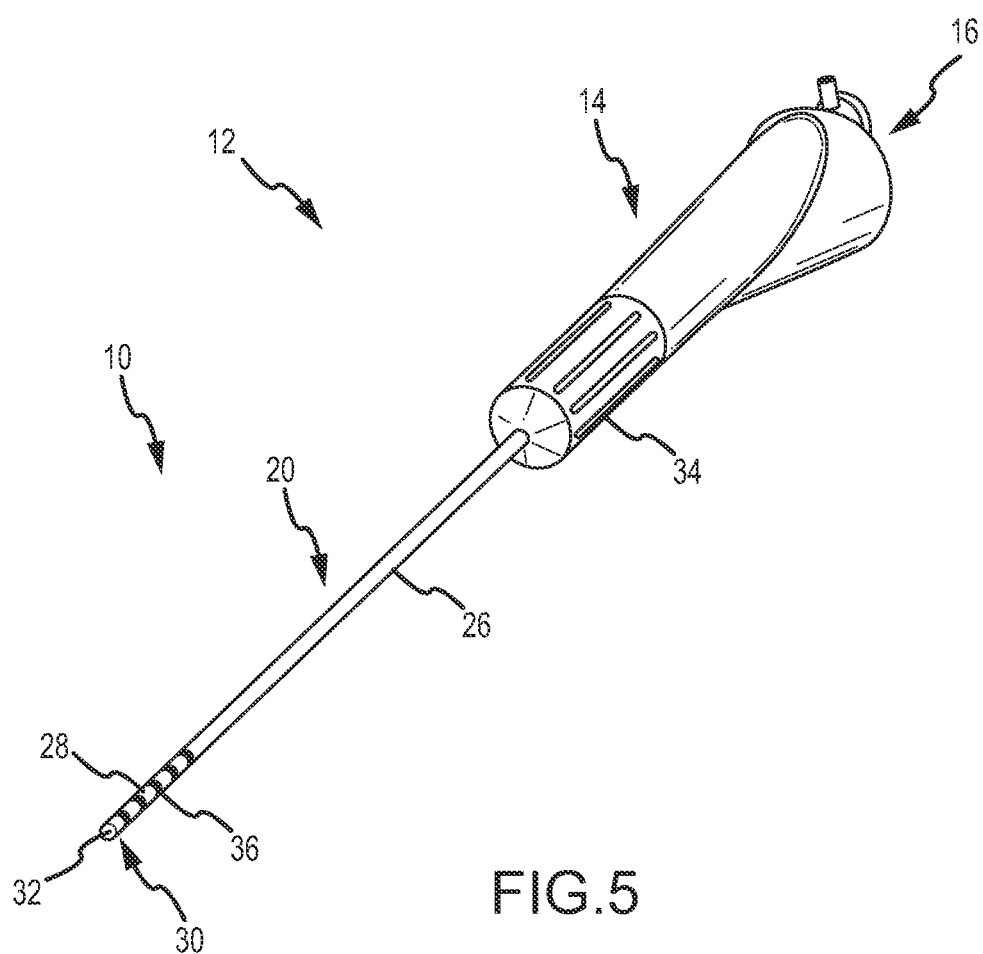
FIG. 5 is an isometric view of steerable sheath access device according to an embodiment of the present invention.
Figure 6:
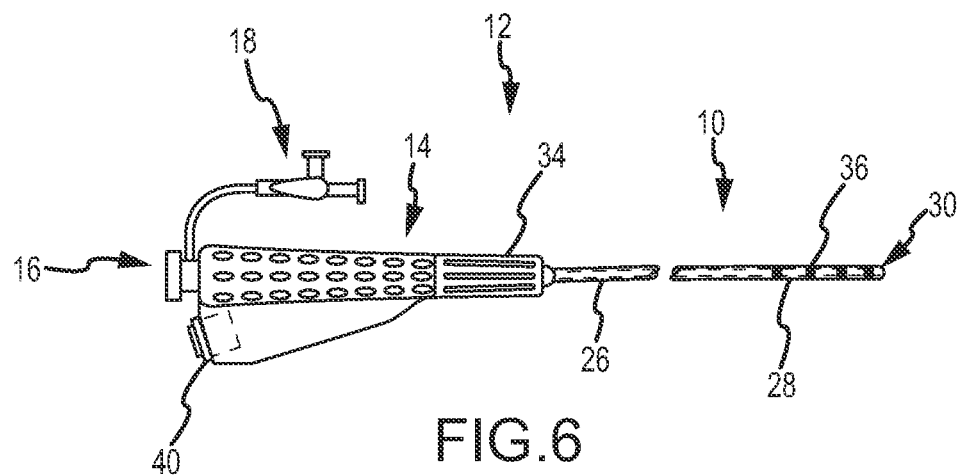
FIG. 6 is an isometric view of steerable sheath access device according to an embodiment of the present invention.
Figure 7:
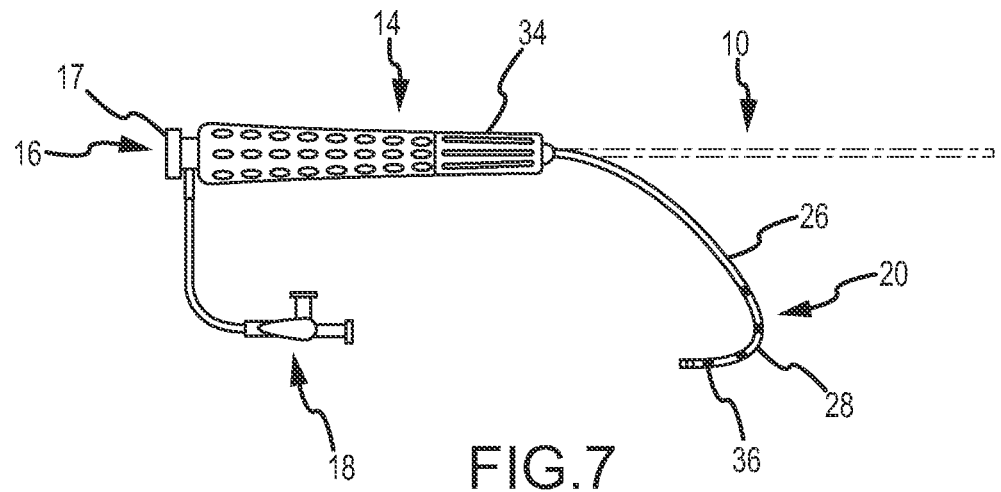
FIG. 7 is an isometric view of steerable sheath access device according to an embodiment of the present invention showing the original position of the access sheath in phantom.

In FIGS. 5-7, alternate embodiments of sheath access device 10, shown connected to handle assembly 14 as part of steerable sheath access device assembly 12, are provided. FIGS. 5-7 further disclose an embodiment of a sheath 10 that further includes a plurality of ring electrodes 36 disposed on the outer surface about distal section 28 of elongated member 20. Ring electrodes 36 may be provided in a number of combinations and distributed along distal section 28 of elongated member 20, so long as not to prevent or impede the primary curve configured by distal section 28 of sheath 10, as shown in FIG. 7. Ring electrodes 36 may be used for mapping or ablation or any other type of procedure that might involve the incorporation of ring electrodes on the outer surface of distal section 28 of sheath 10. Ring electrodes 36 may be used for mapping or visualization of the tissue surface such that the information received from the mapping electrodes may be transmitting to a visualization or mapping processor or system, such as those found and used by the ENSITE® NavX Navigation and Visualization Technology, referred to as the ENSITE® system developed by St. Jude Medical, Inc.

FIG. 5 provides a steerable sheath access device assembly 12 having sheath 10 in a fully extended position/configuration. Accordingly, the deflection portion 34 of handle assembly 14 has not been rotated to exert force or tension on the pull wires internal to elongated member. Overall, traditional handle assemblies used for sheath or other catheter assemblies may be incorporated for use with the present invention. Accordingly, either a unidirectional or a bidirectional handle may be used to control the deflection of sheath 10.

FIG. 6 further provides an alternate view of an embodiment of the present invention including mapping electrodes 36 and further providing an electrical connector 40 for supplying electrical energy to handle assembly 14 and ultimately to mapping electrodes 36 provided on distal section 28 of elongated member 20.

FIG. 7 illustrates the deflection of proximal section 26 and distal section 28 of the sheath 10. The distal section 28 may include, for example, one or more mapping electrodes 36. In accordance with an embodiment of the present invention, the primary curve provided by the deflection of distal section 28 has a smaller (and typically significantly smaller) inner radius than the inner radius corresponding to the secondary curve provided by the deflection of proximal section 26 of elongated member 20 of sheath 10.

The short access sheath 10 as provided and described above is steerable through the incorporation of and use of pull wires that extend from handle assembly 14, as shown in FIG. 1, through elongated body 20 of sheath 10. In one embodiment, a single set of pull wires, i.e. 2-4 pull wires, are provided and disposed within sheath 10 for deflecting the sheath 10 and creating the primary and secondary curves. In an embodiment, each pull wire may be separated by from 90-180 degrees from one another and may be integrated within elongated member 20 so as to extend to the region where distal section 28 intersects with distal tip portion 30. Accordingly, as rotation force from deflection member 34 of handle assembly 14 is applied, the pull wires undergo force which results in the deflection of proximal section 26 and distal section 28. Upon the application of force on the distal ends of pull wires, provided within distal section 28 of sheath 10, distal section 28 comprised of a less rigid material deflects at a great angle therein defining a smaller radius of curvature in comparison to the secondary curvature defined by proximal section 26.

Figure 8:
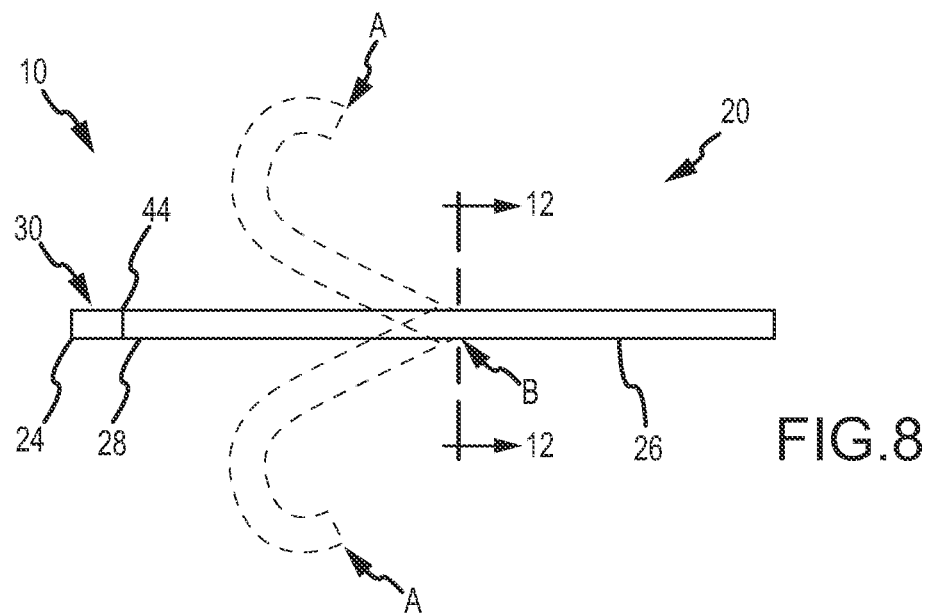
FIG. 8 is an illustrative drawing showing the deflection points of the access sheath in accordance with an embodiment of the present invention.
Figure 9:
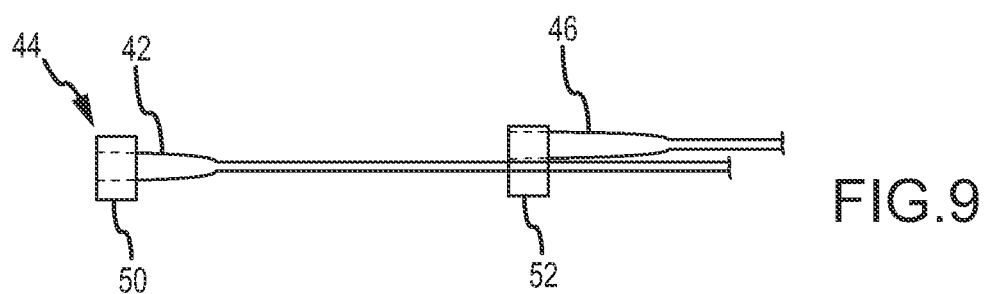
FIG. 9 is an illustrative drawing of pull wires associated with the access sheath in accordance with an embodiment of the present invention.
Figure 10:
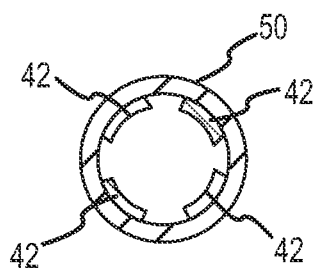
FIGS. 10 and 11 are cross-sectional views of anchor rings provided within a steerable sheath access device in accordance with an embodiment of the present invention.

FIGS. 8-12 illustrate an alternate embodiment of access sheath 10 wherein two sets of pull wires are incorporated within elongated member 20 and positioned to separately acuate deflection of distal section 28 at a primary deflection point (A) and proximal section 26 at a secondary deflection point (B), independently. In particular, FIG. 8 is an illustrative drawing showing sample deflection points (A, B) of access sheath 10 in accordance with an embodiment of the present invention. Moreover, FIG. 9 provides a corresponding illustration of pull wires associated with the access sheath in accordance with the embodiment of access sheath 10, for example as shown in FIG. 8. The deflection of distal section 28 may be controlled by a primary set of pull wires 42 which extend along elongated member to the distal end of distal section 28. Primary pull wires 42, such as shown in FIG. 9, may be secured to distal end 44 of distal section 28 by a member such as an anchor ring 50, which may be configured as generally shown in FIG. 10. A secondary set of pull wires 46 extends along elongated member 20 to at or about the point where distal section 28 intersects with proximal section 26. Secondary pull wires 46 may be secured to the elongated member of sheath 10 by an anchor ring 52 as that shown in FIG. 11. Although only distal section 28 is shown as deflected in FIG. 8, proximal section 26 may deflect therein to provide a primary curve formed by distal section 28 and a secondary curve formed by proximal section 26. As previously described, distal section 28 includes a material that is comparatively more flexible and is less rigid that the material of proximal section 26. As a result, even with primary pull wires 42 to control and acuate the deflection of distal section 28, and secondary set of pull wires 46 control and acuate the deflection of proximal section 26, the inner radius ($r_1$) of curvature of distal section 28 is less than the inner radius of curvature ($r_2$, $r_3$) of proximal section 26.

Figure 11:
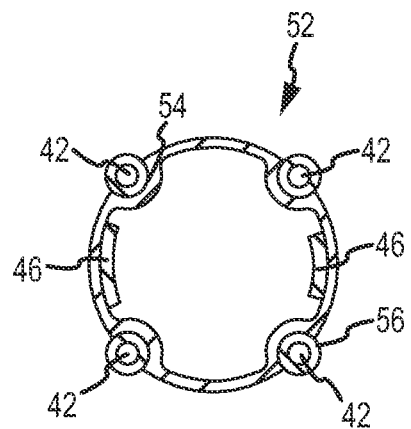

FIGS. 10 and 11 provide illustrative views of the anchor rings 50, 52 used to secure primary pull wires 42 and secondary pull wires 46 within elongated member 20 of sheath 10. As previously discussed, anchor ring 50 is positioned at distal end 44 of distal section 28. Anchor ring 50 is generally cylindrical and may reflect the size and/or shape of elongated member 20 such that anchor ring 50 fits within elongated member and may be reflowed into position once primary pull rings are secured to anchor ring 50 through attachment mechanisms known in the industry. As seen in FIG. 11, anchor ring 52 may comprise a clover-like design and can be provided with recessed grooves 54 for receiving primary pull wires 42 and secondary pull wires 46. In an embodiment anchor ring 52 is positioned at the secondary deflection point wherein proximal section 26 intersects with distal section 28. In one embodiment, pull wires may be stainless steel, such as for example the 304 type, and may be either round or rectangular in cross section. In another embodiment, nitinol wire may be used as pull wires.

Figure 12:
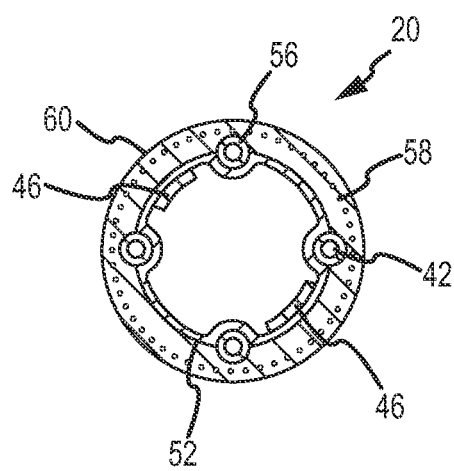
FIG. 12 is a cross-sectional view of the steerable sheath access device in accordance with an embodiment of the present invention.

FIG. 12 shows a cross-sectional view of steerable sheath access device 10 in accordance with an embodiment of the present invention as taken along lines 12-12 of FIG. 8 at the secondary deflection point. The pull wires may, for example, be encased in a polyimide or Teflon guide tubing 56. Secondary pull wires 46 can be secured to anchor ring 52 through various attachment mechanisms as known in the art. Access sheath 10 further comprises an outer body 58 of thermoplastic material that can he provided in a. braided configuration to achieve the flexibility and desired hardness of the proximal and distal sections 26, 28. An outer coating of (e.g. PEBAX®) may then be provided to create an outer surface 60 of elongated member 20 of sheath 10.

Access sheath device 10 as previously described in the various embodiments may be provided as part of an assembly or kit which provides and incorporates the use of various tools and devices that correspond or are appropriately configured for a given size of access sheath 10. Because it may be desirable to have a shortened access device, it may be further desirable to include various medical tools that may be inserted within the inner lumen of access sheath 10 for procedures on the epicardial surface of the heart.

In particular, various catheters, including RF ablation catheters, such as the medium-sweep Safire cooled directional catheter, may be included to have a shortened catheter shaft (e.g. ranging from 30-35 inches in length, such that the catheter shaft may be readily incorporated within access sheath for performing ablative procedures. Other types of energy sources may also be used in connection with access sheath device 10 of the present invention, such as ultrasound (e.g. HIFU), laser, or other energy used for performing ablative procedures. Additional electrode tips may be used and configured, such as a closed loop cooled tip, for incorporation with the shorted catheter assembly for insertion within access sheath device 10.

Additional medical devices for incorporation in the access sheath include a dilator exhibiting an increased softer shaft, similar to the hardness of the material comprising distal section 28 of elongated member 20, described above. The dilator may include a blunt nose tip and to shortened shaft. The device could include several dilators a rather stiff device which is used to access the pericardial space, a softer tipped device to aid in pericardial navigation and finally a soft blunt tipped dilator which is used to plug sheath when device is left in position for extended periods of time while physician performs endocardial procedure. The dilator may further provide a soft closed nosed dilator that may be used after access to the pericardial sac is gained and the access sheath is left in position while other procedures are being performed, in order to aid in keeping pericardial fluid in the area. In an embodiment, the dilator is provided to open the needle puncture in the pericardium and provide a smooth transition between the guidewire and the sheath outside diameter.

A Touhy needle may also be used to gain access to t he pericardial sac, more particularly for example a 17 ga×4.5" long needle (e.g. Soda technique). A guidewire may also be used, such as a long floppy tip guidewire. Each of these components may aid in the physician being able to access, and ablate in, the pericardial space using radiofrequency techniques, although other energy sources may he used.

An assembly or kit for use in treating atrial fibrillation through performing ablative procedures on the epicardial surface of the heart may include shortened steerable access sheath device 10, as such described in accordance with the multiple embodiments of the present invention.

Although a number of embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A steerable introducer, comprising:
   an elongated member having a longitudinal axis and defining a cross-sectional area transverse to the longitudinal axis, the elongated member comprising an open-ended distal tip portion, a distal portion defining a first curve, a proximal portion defining a second curve, and a lumen extending along the longitudinal axis between the proximal portion and the open-ended distal tip portion, wherein the lumen comprises a majority of the cross-sectional area and defines a passageway through which a medical device may pass and exit the elongated member;
   an electrode coupled to the distal portion of the elongated member; and
   a handle assembly coupled to the proximal portion of the elongated member, the handle assembly comprising:
   a body; and
   a deflection member movably coupled to the body and operably coupled to the elongated member such that movement of the deflection member relative to the body causes the elongated member to deflect;
   a first pull wire extending from the handle assembly through at least a substantial portion of the proximal portion of the elongated body and operably coupled to the deflection member such that a first movement of the deflection member relative to the body of the handle assembly exerts a first force on the first pull wire; and
   a second pull wire extending from the handle assembly through at least the substantial portion of the proximal portion of the elongated body and operably coupled to the deflection member such that a second movement of the deflection member relative to the body of the handle assembly exerts a second force on the second pull wire,
   wherein the first pull wire and the second pull wire are configured to separately actuate the distal portion at a primary deflection point and the proximal portion at a secondary deflection point.

2. The steerable introducer of claim 1, further comprising a plurality of electrodes coupled to the distal portion of the elongated member.

3. The steerable introducer of claim 1, further comprising a valve assembly coupled to a proximal end of the handle assembly, wherein the valve assembly comprises an aperture coupled to an inner cavity of the handle assembly, and wherein the inner cavity is coupled to the lumen of the elongated member such that the aperture, inner cavity, and lumen define the passageway through which the medical device may pass and exit the elongated member.

4. The steerable introducer of claim 1, further comprising an electrical connector coupled to the handle assembly, wherein the electrical connector is electrically coupled to the electrode.

5. The steerable introducer of claim 4, wherein the electrical connector is configured to be connected to a visualization or mapping system.

6. The steerable introducer of claim 1, wherein the open-ended distal tip portion is tapered or chamfered.

7. The steerable introducer of claim 1, wherein the distal portion of the elongated member is more flexible than the proximal portion of the elongated member.

8. The steerable introducer of claim 1, wherein the elongated member comprises a thermoplastic material, wherein the thermoplastic material is braided.

9. The steerable introducer of claim 1, wherein the lumen is surrounded by a lining configured to reduce friction when a medical device is inserted into the lumen.

10. The steerable introducer of claim 1, wherein when the elongated member is in a fully extended configuration, the deflection member may be moved in only one direction.

11. The steerable introducer of claim 1, wherein when the elongated member is in a fully extended configuration, the deflection member may be moved in two directions.

12. The steerable introducer of claim 1, wherein the deflection member is rotatable with respect to the body of the handle assembly.

13. The steerable introducer of claim 1, wherein the first pull wire is encased inside a guide tubing.

14. The steerable introducer of claim 1, wherein the first pull wire is positioned between an inner and an outer layer of the elongated member.

15. The steerable introducer of claim 1, wherein the first and second pull wires comprise four pull wires, including a primary pair of pull wires and a secondary pair of pull wires, wherein the primary pair of pull wires extends from the handle assembly through the proximal and distal portions of the elongated body to a distal end of the distal portion, wherein the secondary pair of pull wires extends from the handle assembly through the proximal portion of the elongated body to a point where the distal portion intersects the proximal portion, wherein each pull wire of the primary pair of pull wires is operably coupled to the deflection member such that movement of the deflection member relative to the body of the handle assembly exerts a force on at least one pull wire of the primary pair of pull wires, and wherein each pull wire of the secondary pair of pull wires is operably coupled to the deflection member such that movement of the deflection member relative to the body of the handle assembly exerts a force on at least one pull wire of the secondary pair of pull wires.

16. A deflectable medical device, comprising:
   a shaft having a longitudinal axis and defining a cross-sectional area transverse to the longitudinal axis, the shaft having a proximal end, a distal end, an open-ended distal tip portion, and a major lumen disposed therein and extending between the proximal end and the open-ended distal tip portion, the shaft being configured to receive a second medical device therein, the shaft further comprising:
   an inner liner having an inner surface and an outer surface, the inner surface forming the major lumen, wherein the major lumen comprises a majority of the cross-sectional area; and
   an outer layer comprising a polymeric material adjacent the outer surface of the inner liner;

means for deflecting the shaft in at least one direction relative to a longitudinal axis of the shaft coupled to a proximal portion of the shaft; and an electrode mounted on the shaft, wherein the means for deflecting the shaft comprises a primary deflection point in a distal section of the shaft and a secondary deflection point in a proximal section of the shaft.

17. The medical device of claim 16, wherein the outer layer further comprises a braided wire assembly.

18. The medical device of claim 16, wherein the means for deflecting the shaft comprises four deflectable elements disposed within the outer layer of the shaft and offset from each other by 90 degrees.

19. The medical device of claim 16, wherein the outer layer of the shaft comprises a plurality of portions having different durometers.

20. The steerable introducer of claim 13, wherein the elongated member further comprises an outer body, and wherein the guide tubing is at least partially embedded into an inner surface of the outer body.

21. The steerable introducer of claim 15, wherein the handle is configured such that (i) movement of the deflection member that exerts a force on at least one pull wire of the primary pair of pull wires changes the first curve, and (ii) movement of the deflection member that exerts a force on at least one pull wire of the secondary pair of pull wires changes the second curve.

* * * * *